(12) United States Patent
Scholz et al.

(10) Patent No.: US 6,303,535 B1
(45) Date of Patent: Oct. 16, 2001

(54) PROCESS FOR REDUCING OXIDIC HYDROGENATION CATALYSTS

(75) Inventors: Bernhard Scholz; Alfred Kaizik, both of Marl; Wilfried Büschken, Haltern, all of (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/617,268

(22) Filed: Jul. 17, 2000

(30) Foreign Application Priority Data

Jul. 16, 1999 (DE) ................................. 199 33 348

(51) Int. Cl.[7] ............................. B01J 23/00; B01J 23/72; B01J 23/70; B01J 31/00
(52) U.S. Cl. .................. 502/315; 502/318; 502/319; 502/331; 502/337; 502/345; 502/172; 502/173
(58) Field of Search ......................... 502/315, 318, 502/319, 331, 337, 345, 172, 173

(56) References Cited

U.S. PATENT DOCUMENTS

| | | | |
|---|---|---|---|
| 3,900,429 | * 8/1975 | Komatsu et al. | 252/462 |
| 3,925,259 | * 12/1975 | Kane | 423/213.2 |
| 3,925,490 | * 12/1975 | Reich et al. | 260/643 B |
| 4,234,462 | * 11/1980 | Bondar et al. | 252/881 |
| 4,358,361 | * 11/1982 | Peters | 208/89 |
| 4,762,817 | * 8/1988 | Logsdon et al. | 502/329 |
| 4,780,300 | * 10/1988 | Yokoyama et al. | 423/415 |
| 4,808,562 | 2/1989 | Kubersky et al. | 502/172 |
| 4,960,960 | * 10/1990 | Harrison et al. | 568/881 |
| 5,004,845 | * 4/1991 | Bradley et al. | 568/885 |
| 5,030,609 | 7/1991 | Turner et al. | 502/318 |
| 5,093,535 | * 3/1992 | Harrison et al. | 568/881 |
| 5,523,500 | * 6/1996 | Cheminal et al. | 570/169 |
| 5,534,475 | * 7/1996 | Miramontes Cardenas et al. | 502/304 |

FOREIGN PATENT DOCUMENTS

| | | |
|---|---|---|
| 1768313 | 4/1971 | (DE) . |
| 3443277 A1 | 6/1985 | (DE) . |
| 3524330 A1 | 1/1987 | (DE) . |
| 0850 905 A1 | 7/1998 | (EP) . |
| 385625 | 1/1933 | (GB) . |
| WO 95/19844 | 7/1995 | (WO) . |

* cited by examiner

*Primary Examiner*—Mark L. Bell
*Assistant Examiner*—Patricia L. Hailey
(74) *Attorney, Agent, or Firm*—Oblon, Spivak, McClelland, Maier & Neustadt, P.C.

(57) ABSTRACT

A nickel-containing hydrogenation catalyst is prepared by reducing nickel-containing catalyst material in the liquid phase in a single-stage process by means of hydrogen.

3 Claims, No Drawings

PROCESS FOR REDUCING OXIDIC HYDROGENATION CATALYSTS

BACKGROUND OF THE INVENTION

1. Field of the Invention

The present invention relates to a process for reducing oxidic hydrogenation catalysts and to a process for hydrogenating aldehydes over the reduced catalysts to form alcohols. More particularly, the invention relates to the alcohols prepared by the hydrogenation reaction.

2. Discussion of the Background

Alcohols can be prepared by catalytic hydrogenation of aldehydes which, for example, have been obtained by hydroformylation of olefins or by the aldol condensation reaction. Large amounts of alcohols are used as solvents and as intermediates for the preparation of many organic compounds. Important downstream products of alcohols are plasticizers and detergents.

It is known that aldehydes can be reduced catalytically with hydrogen to form alcohols. In such reduction reactions, catalysts which comprise at least one metal selected from groups 1b, 2b, 6b, 7b and/or 8 of the Periodic Table of the Elements are frequently employed. The hydrogenation of aldehydes can be conducted continuously or batchwise in the gas or liquid phase using pulverulent or shaped catalysts. For the industrial preparation of alcohols by hydrogenation of aldehydes, preference is given, especially in the case of high-volume products, to continuous processes using fixed-bed catalysts in the gas or liquid phase. Compared to gas-phase hydrogenation, liquid-phase hydrogenation has the more favorable energy balance. This advantage increases with increasing molar weight of the aldehyde to be hydrogenated. Higher aldehydes having more than 7 carbon atoms are, therefore, preferably hydrogenated in the liquid phase.

The hydrogenation catalysts normally used in industry are produced by reduction of appropriate precursors which contain the catalytically active metals in oxidic or salt-like form. Hydrogenation catalysts which have been activated in this manner are very reactive and are rapidly oxidized in air; some are even pyrophoric.

The reduction of the catalyst precursors should, in order to keep the start-up times or down-times of a hydrogenation reactor as short as possible, occur as quickly as possible but without impairing the activity and/or operating life of the catalyst.

The reduction of catalyst precursors arranged in a fixed bed to give the actual active metal-containing catalyst species is a step which has a critical influence on the success of the subsequent hydrogenation process. During the reduction of the metal compounds present in the catalyst precursor, heat is liberated. This amounts, for example, to 20 kcal/mol in the reduction of CuO to Cu. Overheating of the precursor or the catalyst during the reduction has to be prevented because otherwise thermal damage to the catalyst, e.g. enlargement of the metal crystallites, occurs. In order to obtain a hydrogenation catalyst having an optimum activity and a high strength, the reduction has to be conducted under extremely careful temperature control.

The reduction of catalyst precursors can be conducted in a liquid phase or a gas mixture.

In the absence of a liquid phase, the catalyst precursor is frequently reduced with a gas mixture consisting of hydrogen and an inert gas, preferably nitrogen. The gas-phase reduction of a copper catalyst is described in JP 61-161146. Reduction of Cu/Zn catalysts is known as disclosed in DE 17 68 313 and DE 34 43 277. JP 1-127042 discloses the gas-phase reduction of Cu/Cr catalysts.

Because of the low heat capacity of gas mixtures, reduction can be conducted only slowly and/or a very high gas hourly space velocity (GHSV) has to be set to ensure removal of heat. Reduction using a high gas hourly space velocity produces large amounts of gas which have to be disposed of. Because of the high inert gas content of the gas mixture, working-up of the gas to recover hydrogen is not worthwhile. The high gas hourly space velocity can be achieved more economically by circulating the gas with the aid of a circulating gas blower.

As an alternative to gas-phase reduction, the catalyst precursor can be reduced in the presence of a liquid phase. Here, the heat of reduction is removed by means of the liquid.

As disclosed in GB 385 625, a Cu/Cr catalyst precursor is reduced in the presence of a carboxylic ester at a liquid hourly space velocity (LHSV) of 8 $h^{-1}$. JP 47-14113 describes the activation of a Cu/Cr catalyst in a stream of lactone (LHSV=0.67 $h^{-1}$) at 200° C. Another method of reducing Ni/Cu/Mo or Co/Cu catalyst precursors is disclosed in DE 35 24 330. Here, reduction is conducted at 200° C. and 250 bar in a stream of isopropanol at a throughput per unit cross-sectional area of 60 $m^3/(m^2 \cdot h)$ for an Mo-containing catalyst and of 30 $m^3/(m^2 \cdot h)$ for a Co-containing catalyst.

These reduction processes have the disadvantage that they employ high temperature and/or pressures and require long reaction times up to a number of days.

Still another process for reducing hydrogenation catalysts is described in EP 0 689 477. Here, copper-containing catalyst precursors, in particular Cu/Cr, Cu/Zn, Cu/Fe, Cu/Al and Cu/SiO$_2$, are reduced in the liquid phase in a two-stage process. The liquid phase can comprise esters, alcohols or hydrocarbons. The two-stage process of EP 0 689 477 employs a temperature program in which at least 10% by weight of the copper is reduced in the first stage at a temperature ranging from 20 to 140° C. In the second stage, the temperature is increased from 140 to 250° C. Disadvantages are the complicated temperature control and the still long reduction time of, on average, 40 hours. A need continues to exist for a method of effectively reducing catalyst precursors without impairing the resultant catalyst.

SUMMARY OF THE INVENTION

Accordingly, one object of the present invention is to provide a process for reducing catalyst precursors by means of which short reduction times can be achieved without the activity of the resulting catalyst being impaired, particularly where the catalyst is employed in the hydrogenation of aldehydes to alcohol product.

Briefly, this object and other objects of the present invention as hereinafter will become more readily apparent can be attained by a process for reducing a nickel-containing catalyst, which comprises:

reducing a nickel-containing catalyst material in the liquid phase in a single-stage process by means of hydrogen, thereby producing a nickel-containing catalyst useful for the hydrogenation of aldehydes.

DETAILED DESCRIPTION OF THE PREFERRED EMBODIMENTS

It has now been found that the reduction of a catalyst precursor can be conducted in a short time in the presence of a solvent at elevated temperature and moderate pressure in a liquid-phase hydrogenation unit without loss of activity and that the resulting catalysts are very suitable for the preparation of alcohols.

The present invention accordingly provides a process for reducing nickel-containing catalysts for aldehyde hydrogenation, in which the reduction is conducted in the liquid phase in a single-stage process by means of hydrogen.

The process of the present invention has a number of advantages which include that the reduction of the catalyst precursor can be conducted under gentle conditions in a liquid-phase hydrogenation unit, so that optimum activity and strength of the catalyst are obtained. No circulating gas blower is necessary for conducting the reduction reaction, so that no additional capital costs are incurred. The reduction can be conducted in less than 24 hours, which significantly shortens the downtime of the hydrogenation plant when changing the catalyst compared to other reduction processes. The catalyst is formed in the low pressure range from 1 to 25 bar, so that no additional high-pressure resistant vessels or reactors are necessary.

A single-stage reduction in the sense of the present invention employs fixed reaction parameters. Thus, pressure and temperature are fixed and not changed subsequently in any step. Heat can be supplied, for example, by means of an appropriately heated liquid phase. The reduction is conducted by means of hydrogen; it is also possible to use hydrogen-containing mixtures. The reduction of the nickel-containing catalysts can be conducted in the same reactor as the subsequent aldehyde hydrogenation.

To hydrogenate aldehydes by means of the process of the invention in the liquid phase, it is possible to use pelletized or shaped, fixed-bed catalysts which are prepared by reduction by the invention of corresponding precursors. Suitable precursors can comprise the metals of groups 1b, 2b, 6b, 7b and/or 8 of the Periodic Table, in particular nickel, copper and chromium. Catalysts applied to supports or unsupported catalysts can be used. Unsupported catalysts generally comprise from about 0.2 to 30% by weight of nickel, from 25 to 40% by weight of copper and from 18 to 40% by weight of chromium. The catalysts can further comprise up to 20% by weight of basic substances such as alkali metal or alkaline earth metal oxides or hydroxides, and also other inert or property-modifying materials in the same amounts, for example, graphite.

Preferred catalysts in the process of the invention for hydrogenating aldehydes to give alcohols are supported catalysts. They comprise from 0.3 to 15% by weight of copper and from 0.3 to 15% by weight of nickel and also, as activators, from 0.05 to 3.5% by weight of chromium and advantageously from 0.01 to 1.6% by weight of an alkali component on a support material. The support material preferably comprises aluminum oxide or silicon oxide. The amounts indicated are based on the unreduced catalyst, i.e. the catalyst precursors.

The catalyst precursors, i.e., the unreduced catalysts, are advantageously used in a form which offers a low resistance to flow, e.g., in the form of granules, pellets or shaped bodies such as tablets, cylinders, extrudates or nogs.

According to the invention, the reduction of the catalyst precursor occurs in the presence of a liquid phase which can serve as a heat transfer medium. A suitable liquid phase is a liquid organic material which does not dissolve any component from the catalyst precursor, causes no structural change to the catalyst, undergoes no reactions with the metal components or the support material and does not irreversibly occupy the active sites of the catalyst. Suitable materials include, for example, hydrocarbons, esters, lactones and alcohols which are liquid under the reaction conditions. It is also possible to use solvent mixtures consisting of, for example, hydrocarbons and alcohols or of a plurality of different alcohols.

The liquid phase preferably comprises alcohols or alcohol mixtures, particularly preferably alcohols having from 6 to 25 carbon atoms. In a preferred embodiment of the invention, the liquid phase comprises alcohol product from an aldehyde hydrogenation reaction.

The aldehyde starting material to be hydrogenated can be prepared by hydroformylation of olefins, e.g. as described in DE 196 54 340.1. The aldehyde starting material can also be prepared by aldol condensation, e.g., of butyraldehydes or valeraldehydes. Suitable examples of aldehydes which can be hydrogenated using the catalyst reduced by the process of the invention include butyraldehyde, valeraldehyde, hexanal, heptanal, octanals, octenals such as 2-ethylhex-2-enal, isononanals, decanals, decenals, tridecanals and the like.

The liquid phase used preferably comprises the hydrogenation products of these aldehydes, e.g., butanol, 2-ethylhexanol, isononanol, isodecanol or tridecanol.

The time for reduction of the catalyst precursors in the process of the invention is generally less than 24 hours and is thus considerably shorter than known processes. The LHSV of one of the above-mentioned liquids over the catalyst precursor can range from 0.1 to 10 $h^{-1}$, preferably from 1 to 5 $h^{-1}$. At these space velocities, the liquid flows uniformly around the catalyst precursor. This measure improves heat transfer from the catalyst precursor to the liquid so that local overheating of the catalyst precursor ("hot spots") can be ruled out.

The reducing gas used in the process of the invention comprises an inert gas, preferably nitrogen, and hydrogen. The hydrogen content of the gas mixture can be increased during the reduction starting from pure inert gas, so that uniform reduction of the catalyst precursor is achieved. The proportion by volume of hydrogen in the gas can increase from 0 to 100% by volume; the hydrogen concentration preferably ranging from 20 and 80% by volume.

In the process of the invention, the gas hourly space velocity (GHSV) ranges from 1 to 50 $h^{-1}$, preferably from 2 to 10 $h^{-1}$. The major part of the water of reaction is carried out of the reaction system together with the waste gas.

The reduction of the catalyst precursor is preferably conducted at the same pressure as or at a lower pressure than the subsequent aldehyde hydrogenation. The pressure preferably ranges from 1 to 25 bar, i.e. in the low pressure range. When using a liquid phase having a boiling point at atmospheric pressure, which is higher than the reduction temperature, the reduction is preferably conducted at a pressure ranging from 1 to 2 bar. If the liquid phase employed is a liquid or liquid mixture having a low boiling point at atmospheric pressure, the pressure has to be increased so that the solvent employed is present in liquid form in the reactor and only little of it is lost with the waste gas.

The reduction of the catalyst precursor can be conducted in the temperature range of 100 to 200° C., preferably 130 to 170° C., and a pressure of 1 to 25 bar, preferably 1 to 10 bar.

The reduction time is dependent on the conditions selected. The course of the reduction is followed by means of the water balance and the reduction time is generally less than 24 hours, preferably from 6 to 18 hours. The catalysts prepared in this manner are suitable for the hydrogenation of aldehydes or aldehyde mixtures, in particular aldehydes or aldehyde mixtures which have been prepared by hydroformylation of olefins or by aldol condensation.

The present invention, therefore, also provides a process for preparing alcohols having from 2 to 20 carbon atoms by hydrogenation of the corresponding aldehydes over nickel-containing catalysts, in which the nickel-containing catalysts are reduced in the liquid phase in a single-stage process by means of hydrogen prior to the hydrogenation of the aldehydes.

Furthermore, the invention provides for the use of the alcohols prepared by the process of the invention as plasticizer alcohols or in detergents.

The aldehydes to be hydrogenated can be obtained by hydroformylation of olefins. It is possible to use aldehydes which have already been purified, but the reactor output from the hydroformylation, if appropriate after separating the catalyst phase, i.e. a mixture of aldehydes, alcohols, olefins and/or high boilers, can also be employed in the hydrogenation process of the invention.

The aldehydes can, as already indicated, be prepared by hydroformylation of olefins or aldol condensation. The aldehydes and thus the alcohols preferably have from 2 to 20, particularly preferably from 4 to 16, carbon atoms. Very particularly preferred aldehydes are $C_4$-, $C_5$-, $C_8$-, $C_9$- and $C_{13}$-aldehydes. The aldehydes can be aliphatically saturated or unsaturated. The reduction reaction of the invention of α,β-unsaturated aldehydes leads to completely saturated alcohols; thus, 2-ethylhex-2-enal is hydrogenated to 2-ethylhexanol. In the reduction of olefinically unsaturated aldehydes having double bonds which are not conjugated with the aldehyde functional group, only the aldehyde functional group is hydrogenated while the olefinic double bonds are largely retained.

In the process of the invention for preparing alcohols by hydrogenation of the corresponding aldehydes over nickel-containing catalysts, the liquid phase employed in the reduction of the catalyst can comprise alcohols, preferably alcohols obtained from the hydrogenation of aldehydes.

If the liquid phase comprises alcohols, these can, of course, be identical to the alcohols produced by the hydrogenation of the aldehydes.

If, for example, isononanal is hydrogenated to isononanol over a catalyst activated by the process of the invention, the liquid phase employed for the reduction of the catalyst advantageously also comprises isononanol.

The preparation of alcohols by the process of the invention, i.e., the hydrogenation of aldehydes, can be conducted in the same reactor as the reduction of the nickel-containing catalysts.

The reduction of the nickel-containing catalyst which is conducted prior to the hydrogenation can be conducted at a temperature ranging from 100 to 200° C., preferably from 130 to 170° C., and a pressure ranging from 1 to 25 bar, preferably 1 to 10 bar.

For the liquid-phase hydrogenation of the aldehydes or the hydroformylation mixtures, a variety of process variants can be selected. The hydrogenation can be conducted adiabatically or virtually isothermally, i.e., with a temperature increase of <10° C., in one or two stages. In the latter case, both reactors, advantageously tube reactors, can be operated adiabatically or virtually isothermally or one reactor can be operated adiabatically and the other reactor operated isothermally. Furthermore, it is possible to hydrogenate the aldehyde mixtures in a straight pass or with product recirculation. The reactors can be operated as concurrent reactors with trickle flow or preferably with high liquid hourly space velocities (pulse flow). The liquid-phase hydrogenation of the invention can be conducted under a total pressure ranging from 5 to 25 bar, preferably 15 to 25 bar. If necessary, the hydrogenation mixtures are purified further, e.g., by distillation.

The alcohols prepared using the process of the invention can be used as plasticizer alcohols, e.g. in the form of phthalic diesters, or as detergents.

Having now generally described this invention, a further understanding can be obtained by reference to certain specific Examples which are provided herein for purposes of illustration only and are not intended to be limiting unless otherwise specified.

EXAMPLE 1

Comparative Example

A 10 liter amount of catalyst precursor of a Cu/Cr/Ni-containing supported catalyst was reduced in the absence of a liquid phase:

Composition of the catalyst precursor:

| | |
|---|---|
| 86% $Al_2O_3$ | $AlO_3$ |
| 9% by weight | CuO |
| 4% by weight | NiO |
| 1% by weight | $Cr_2O_3$ |

After introduction of the catalyst precursor, the apparatus was flushed free of oxygen using nitrogen. The apparatus was pressurized with 2 bar of nitrogen, the circulating gas compressor was started up and the apparatus was heated to 150° C. The amount of gas circulated was 3.5 m³/h. During the entire reduction time, nitrogen was taken-off in an amount of 10 liter/h of input and output gas under pressure regulation (2 bar). During the course of the reduction, hydrogen was metered into the apparatus in an increasing amount (see Table 1). The temperature in the contact bed was maintained at 160±5° C.

TABLE 1

Catalyst reduction in the gas phase

| Time in hours | Temperature | Hydrogen in standard l/h | Nitrogen in standard l/h |
|---|---|---|---|
| 0–8 h | 160 | 2.5 | 10 |
| 9–16 h | 161 | 5.0 | 10 |
| 17–24 h | 159 | 7.5 | 10 |
| 25–32 h | 160 | 10.0 | 10 |
| 33–40 h | 161 | 12.5 | 10 |
| 41–48 h | 160 | 15.0 | 10 |
| 49–56 h | 161 | 17.5 | 10 |

The activity of the catalyst which had been reduced in this manner was tested in a circulation reactor. For this purpose, one liter of a reaction product from a Rh-catalyzed hydroformylation of tributene was hydrogenated in the liquid phase at 180° C. and 25 bar absolute over 100 g of the Cu/Cr/Ni catalyst prepared as described above (target product: $C_{13}$-alcohols). The analyses of the starting material and product are shown in Table 2.

TABLE 2

Activity testing of the catalyst reduced in the gas phase

| | 1/LHSV $I_{cat} \cdot h/ I_{starting\ material}$ | Olefins % by weight | Paraffins % by weight | Aldehydes % by weight | Alcohols % by weight | High boilers % by weight |
|---|---|---|---|---|---|---|
| Starting material | 0 | 14.8 | 1.2 | 76.5 | 4.5 | 3.0 |
| Product | 1.75 | 14.3 | 1.7 | 0.3 | 80.4 | 3.3 |

EXAMPLE 2

A 10 liter amount of the catalyst precursor prepared in Example 1 was reduced as follows in the presence of a liquid phase:

The liquid phase was isotridecanol which had been obtained by Rh-catalyzed hydroformylation of tributene and subsequent hydrogenation. Isotridecanol was pumped by means of a circulation pump via a heat exchanger for setting the temperature and through the reactor charged with catalyst precursor.

The circulation flow was 30.0 l/h, corresponding to an LHSV of 3 $h^{-1}$. At a reactor pressure of 2 bar, a constant 30.0 standard l/h of nitrogen was metered in. After reaching 160° C., hydrogen addition was commenced. The initial amount of $H_2$ of 15 standard l/h was increased stepwise to a 60 standard l/h. The water of reaction is partly removed from the reactor with the waste gas, while another part remained in the catalyst bed.

After 10 hours, the reduction of the catalyst precursor was complete (see Table 3).

TABLE 3

Catalyst reduction in the liquid phase

| Time in hours | Temperature | Hydrogen in standard l/h | Nitrogen in standard l/h |
|---|---|---|---|
| 0–1.5 h | 160 | 15 | 30 |
| 1.5–2.0 h | 160 | 20 | 30 |
| 2.0–3.0 h | 160 | 25 | 30 |
| 3.0–5.0 h | 160 | 30 | 30 |
| 5.0–7.0 h | 160 | 35 | 30 |
| 7.0–10 h | 160 | 60 | 30 |

The activity of the catalyst which had been reduced in this manner was subsequently tested under the same conditions as described for the reduced catalyst in Example 1. The analyses of the starting material and product are shown in Table 4.

TABLE 4

Activity determination of the catalyst reduced according to the invention

| | 1/LHSV $I_{cat} \cdot h/ I_{starting\ material}$ | Olefins % by weight | Paraffins % by weight | Aldehydes % by weight | Alcohols % by weight | High boilers % by weight |
|---|---|---|---|---|---|---|
| Starting material | 0 | 14.8 | 1.2 | 76.5 | 4.5 | 3.0 |
| Product | 1.75 | 14.3 | 1.6 | 0.2 | 80.6 | 3.3 |

Tables 2 and 4 show that the activity of the catalyst which has been reduced by the process of the invention corresponds to that of a conventionally activated catalyst. At the same time, the reduction time was able to be reduced to about 18%.

The disclosure of German priority application Serial Number 19933348.3-41 filed Jul. 16, 1999 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process for reducing a nickel-containing catalyst, which comprises: reducing a nickel-containing catalyst material in the liquid phase, which comprises alcohols prepared by the hydrogenation of aldehydes, of a single-stage process by means of hydrogen, thereby producing a nickel-containing catalyst useful for the hydrogenation of aldehydes, wherein the reactor containing the Ni-containing catalyst is also employed for the hydrogenation of aldehydes to alcohol product.

2. The process as claimed in claim 1, wherein the reduction of the nickel-containing catalyst is conducted at a temperature ranging from 100 to 200° C. and a pressure ranging from 1 to 25 bar.

3. The process as claimed in claim 1, wherein the catalyst comprises nickel, copper and chromium.

* * * * *